(12) United States Patent
Shivkumar et al.

(10) Patent No.: US 11,339,296 B2
(45) Date of Patent: May 24, 2022

(54) COMPOUND FOR USE IN COLOUR CHANGE COMPOSITIONS

(71) Applicant: Societe BIC, Clichy (FR)

(72) Inventors: Bagavant Shivkumar, Merseyside (GB); Philippe Marrec, Lannion (FR)

(73) Assignee: Societe BIC, Clichy (FR)

( * ) Notice: Subject to any disclaimer, the term of this patent is extended or adjusted under 35 U.S.C. 154(b) by 454 days.

(21) Appl. No.: 15/757,136

(22) PCT Filed: Sep. 5, 2016

(86) PCT No.: PCT/EP2016/070834
§ 371 (c)(1),
(2) Date: Mar. 2, 2018

(87) PCT Pub. No.: WO2017/037282
PCT Pub. Date: Mar. 9, 2017

(65) Prior Publication Data
US 2018/0244944 A1   Aug. 30, 2018

(30) Foreign Application Priority Data

Sep. 3, 2015   (GB) ...................................... 1515610

(51) Int. Cl.
*C09D 11/00* (2014.01)
*C09B 67/02* (2006.01)
(Continued)

(52) U.S. Cl.
CPC .......... *C09B 67/0097* (2013.01); *C07C 69/78* (2013.01); *C09B 57/00* (2013.01);
(Continued)

(58) Field of Classification Search
USPC ........................ 106/31.01, 31.13, 31.6, 31.64
See application file for complete search history.

(56) References Cited

U.S. PATENT DOCUMENTS

| 3,106,570 A | 10/1963 | Jaruzelski et al. |
| 3,205,270 A | 9/1965 | Jaruzelski et al. |

(Continued)

FOREIGN PATENT DOCUMENTS

| CN | 101558358 | 10/2009 |
| CN | 103079601 | 5/2013 |

(Continued)

OTHER PUBLICATIONS

International Preliminary Report on Patentability dated Mar. 15, 2018 for International Application No. PCT/EP2016/070834.
(Continued)

*Primary Examiner* — James E Mcdonough
(74) *Attorney, Agent, or Firm* — Cook Alex Ltd.

(57) ABSTRACT

Novel reaction media for electron donating and electron accepting components in colour-change compositions are described. The compound is of formula (I): wherein $R_1$, and $R_2$ are selected from a linear or branched alkyl group, alkenyl group, alkoxy group, aryl group and an alkylene aryl group having from 6 to 22 carbon atoms; $X_1$ and $X_2$ are selected from —OC(O)—, —CO$_2$— and O; $R_3$, $R_4$ and $R_5$ are selected from hydrogen and an linear or branched alkyl group, cycloalkyl group, alkenyl group, alkoxy group, aryl and alkylene aryl group; $R_6$ is selected from hydrogen, $R_3$, —$X_1R_1$ and aryl and halogen; $Y_1$ $Y_2$ $Y_3$ and $Y_4$ are selected from hydrogen, $R_3$, —OR$_3$ and halogen; a is 0 to 4; b is 0 or 1; x and y are independently is 0 or 1 provided that where x and y are 0, a is 0 and b is 1 and $R_6$ is —CO$_2R_1$; and wherein when a is 0 and b is 1 and $R_5$ or $R_6$ is phenyl, $R_6$ and $R_5$ respectively are not hydrogen or $C_{1-7}$alkyl. The compounds are useful in ink compositions, writing implements containing the compound and medical and industrial applications in which temperature sensitive colour change may be required.

(Continued)

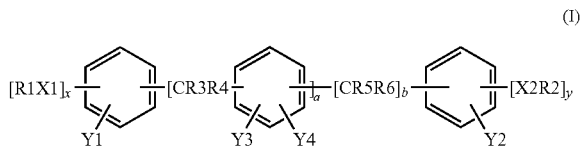

(I)

30 Claims, 2 Drawing Sheets (51) Int. Cl.
| | |
|---|---|
| C09D 11/037 | (2014.01) |
| C09D 11/17 | (2014.01) |
| C09D 11/50 | (2014.01) |
| C09B 57/00 | (2006.01) |
| C09D 5/33 | (2006.01) |
| C09D 5/26 | (2006.01) |
| C09K 9/02 | (2006.01) |
| C07C 69/78 | (2006.01) |
| G01N 21/78 | (2006.01) |
| C09D 1/00 | (2006.01) |
| C09D 4/00 | (2006.01) |
| C09D 5/00 | (2006.01) |
| C09K 3/00 | (2006.01) |

(52) U.S. Cl.
CPC .............. *C09D 5/004* (2013.01); *C09D 5/26* (2013.01); *C09D 11/037* (2013.01); *C09D 11/17* (2013.01); *C09D 11/50* (2013.01); *C09K 9/02* (2013.01); *G01N 21/78* (2013.01); *C09K 2211/1007* (2013.01)

(56) References Cited

U.S. PATENT DOCUMENTS

| | | | |
|---|---|---|---|
| 3,510,431 | A | 5/1970 | Chao et al. |
| 3,979,462 | A | 9/1976 | Krimm et al. |
| 4,188,437 | A | 2/1980 | Rohowetz |
| 4,348,410 | A | 9/1982 | Muramatsu et al. |
| 4,421,560 | A | 12/1983 | Kito et al. |
| 5,755,997 | A * | 5/1998 | Shivkumar ............ C07C 69/92 252/299.65 |
| 5,997,849 | A | 12/1999 | Small et al. |
| 6,280,510 | B1 | 8/2001 | Kelderman et al. |
| 6,326,522 | B1 * | 12/2001 | Nakaguchi ............ C07C 37/16 568/718 |
| 6,992,166 | B2 * | 1/2006 | Nagashima ............ C08G 59/06 523/466 |
| 7,494,537 | B2 | 2/2009 | Ono et al. |
| 8,287,841 | B2 | 10/2012 | Nguyen et al. |
| 8,816,135 | B2 | 8/2014 | Yoshitomo et al. |
| 8,845,799 | B2 | 9/2014 | Fujita |
| 9,309,428 | B2 | 4/2016 | Saito et al. |
| 9,645,494 | B2 | 5/2017 | Kato et al. |
| 9,855,789 | B2 * | 1/2018 | Ono ........................ B43K 5/00 |
| 2010/0075253 | A1 | 3/2010 | Kato et al. |
| 2011/0311460 | A1 | 12/2011 | Nguyen et al. |
| 2013/0061681 | A1 * | 3/2013 | Trahan ..................... A23L 3/003 73/700 |
| 2013/0172183 | A1 | 7/2013 | Kwan |
| 2013/0177703 | A1 | 7/2013 | Clayton et al. |
| 2013/0193386 | A1 * | 8/2013 | Owen ....................... C09D 5/26 252/583 |
| 2013/0210622 | A1 * | 8/2013 | Ono ................... C09B 67/0013 503/213 |
| 2014/0291585 | A1 * | 10/2014 | Tozuka .................. B43K 19/00 252/500 |
| 2015/0322384 | A1 * | 11/2015 | Butterfield ............. C11D 3/42 510/324 |
| 2016/0168011 | A1 * | 6/2016 | Ando ....................... C03C 3/087 501/29 |
| 2016/0289508 | A1 | 10/2016 | Meincke et al. |
| 2017/0274698 | A1 * | 9/2017 | Ono ......................... C09D 11/50 |
| 2018/0251651 | A1 * | 9/2018 | Shivkumar ............. C09D 11/50 |
| 2019/0100656 | A1 * | 4/2019 | Shikumar ............. C09D 11/037 |

FOREIGN PATENT DOCUMENTS

| | | |
|---|---|---|
| CN | 103626958 A * | 3/2014 |
| DE | 908496 | 4/1954 |
| DE | 10326536 A1 | 2/2004 |
| EP | 0242018 A2 | 10/1987 |
| EP | 0426481 A2 | 5/1991 |
| EP | 0677519 A1 | 10/1995 |
| EP | 1061061 B1 | 8/2003 |
| EP | 1375463 A1 | 1/2004 |
| EP | 2424018 A1 | 2/2012 |
| EP | 2468828 A1 | 6/2012 |
| EP | 2527315 A1 | 11/2012 |
| EP | 2772517 A1 | 9/2014 |
| EP | 2772523 A1 | 9/2014 |
| EP | 2500778 B1 | 10/2017 |
| GB | 730890 | 6/1955 |
| GB | 730890 A | 6/1955 |
| GB | 1086404 A | 10/1967 |
| GB | 1390945 | 4/1975 |
| GB | 1390945 A | 4/1975 |
| GB | 730890 * | 6/1995 |
| GB | 2280681 B | 3/1998 |
| JP | S-4858087 A | 8/1973 |
| JP | H05310953 A | 11/1993 |
| JP | H10506939 A | 11/1993 |
| JP | H0641399 A | 2/1994 |
| JP | H0665479 A | 3/1994 |
| JP | H0665479 A | 3/1994 |
| JP | H08259486 A | 10/1996 |
| JP | H09235265 A | 9/1997 |
| JP | H-9235265 A | 9/1997 |
| JP | 2001058968 A | 3/2001 |
| JP | 2003246778 A | 9/2003 |
| JP | 2003246778 A | 9/2003 |
| JP | 2004090231 A | 3/2004 |
| JP | 2004352938 A | 12/2004 |
| JP | 2007118197 A | 5/2007 |
| JP | 2008045062 A | 2/2008 |
| JP | 2010132822 A | 6/2010 |
| JP | 2011256271 A | 12/2011 |
| JP | 2012046655 A | 3/2012 |
| JP | 4934373 B2 | 5/2012 |
| JP | 2013529971 A | 7/2013 |
| JP | 201853096 A | 4/2018 |
| WO | WO 01/04014 A1 | 1/2001 |
| WO | WO 2008/155338 A2 | 12/2008 |
| WO | WO 2010/048067 A2 | 4/2010 |
| WO | 2015/033750 A1 | 6/2010 |
| WO | 2010064447 A1 | 6/2010 |
| WO | WO 2011/065228 A1 | 6/2011 |
| WO | WO 2012/115121 A1 | 8/2012 |
| WO | WO 2013/003538 A1 | 1/2013 |
| WO | 2015074953 A1 | 5/2015 |
| WO | WO 2017/036604 A1 | 3/2017 |
| WO | WO 2017/037284 A1 | 3/2017 |

OTHER PUBLICATIONS

International Search Report dated Dec. 12, 2016 for International Application No. PCT/EP2016/070834.
UK Search Report dated Mar. 4, 2016 for GB Application No. GB1515610.2.
UK Search Report dated Aug. 11, 2016 for GB Application No. GB1515610.2.
Sheryl L. Wiskur et al., "Catalytic Asymmetric Synthesis of Esters from Ketenes", Journal of the American Chemical Society, May 1, 2005, vol. 127, No. 17, pp. 6176-6177.
Carmen Concellon et al., "N-Heterocyclic Carbene-Mediated Enantioselective Addition of Phenols to Unsymmetrical (56) References Cited

OTHER PUBLICATIONS

Alkylarylketenes", Advanced Synthesis & Catalysis, Nov. 1, 2009, vol. 351, No. 17, pp. 3001-3009.

Oe Yohei et al., "Addition Reaction of 2-Phenylbenzoic Acid onto Unactivated Olefins Catalyzed by Ru(II)xantphos Catalysis", Tetrahedron Letters, May 26, 2010, vol. 51, No. 21, pp. 2806-2809.

Shoko Higashi et al., "Synthesis of RuCl2(xantphos)L (L=PPh3, P(OPh)3, DMSO) complexes, and their catalytic activity for the addition of carboxylic acids onto olefins", Journal of Organometallic Chemistry, Aug. 1, 2015, vol. 791, pp. 46-50.

Mirela Matic et al., "Method for Estimating SN1 Rate Constants: Solvolytic Reactivity of Benzoates", The Journal of Organic Chemistry, Oct. 19, 2012, vol. 77, No. 20, pp. 8986-8998.

M. Teresa Barros et al., "Fast Synthesis Employing a Microwave Assisted Neat Protocol of New Monomers Potentially Useful for the Preparation of PDLC Films", Central European Journal of Chemistry, Jun. 4, 2011, vol. 9, No. 4, pp. 557-566.

Anton Vidal-Ferran et al., "Supramolecularly Regulated Ligands for Asymmetric Hydroformylations and Hydrogenations", Chemistry—A European Journal., Aug. 3, 2015, vol. 21, No. 32, pp. 11417-11426.

Roberta B. Hill et al., "Esters and Amides of 2,2'-Diphenic Acid", Journal of Chemical Engineering Data., Apr. 1963, vol. 8, No. 2, pp. 233-234.

Bronislaw P. Czech et al., "Synthesis and solid-state structures of new cyclophane host molecules", Tetrahedron, Feb. 2007, vol. 63, No. 6, pp. 1360-1365.

Stetson, Christopher M.; Nishikawa, Shiro; Purkiss, David W.; Dalley, N. Kent; Bartsch, Richard A.; "Synthesis and evaluation of new ditopic cyclophane receptors for benzoic acid"; Journal of Physical Organic Chemistry, 2005, vol. 18, #11 p. 1107-1115.

Hung, J.; Werbel, L.M.; "Camoform Analogs as Potential Agents Against Mefloquine Resistant Malaria"; European Journal of Medicinal Chemistry, 1983, vol. 18, # 1 p. 61-66.

Chen et al., "Surface Phenomena of Liquid Crystalline Substances", Mol Cryst. Liq Cryst., 1998, pp. 99-116, vol. 325.

Kanji et al., "Synthesis and Mesomorphic Properties of Liquid Crystals with a 5,5'-Bitropolone Skelton", Chem Lett, 2001, pp. 690 to 691, vol. 30.

Kricheldorf et al., "New Polymer Syntheses. 78. Star-Shaped and Hyperbranched Polyesters by Polycondensation of Trimethylsilyl 3,5-Diacetoxybenzoate" Macromolecules, 1995, pp. 2118-2123, vol. 28.

Lin, G et al., "Novel acyl donors for enzyme-catalysed transacylation reactions", Synthetic Communications, Jan. 1993, pp. 2135-2138, vol. 23 No. 15.

\* cited by examiner

COMPOUND FOR USE IN COLOUR CHANGE COMPOSITIONS

CROSS-REFERENCE TO RELATED APPLICATION

This is a U.S. National Stage of International PCT Application Serial PCT/EP2016/070834, filed Sep. 5, 2016 and claims the benefit of priority to Great Britain Application No. 1515610.2 the disclosures of which are hereby incorporated by reference in their entireties.

FIELD OF THE INVENTION

This invention relates to a compound for use in a colour-change composition, preferably a thermochromic composition, a microencapsulated colour material, such as a pigment comprising the colour-change composition and an article comprising the said composition or microencapsulated pigment.

Colour change compositions are widely known and change between a discoloured state and coloured state colour or between a first and second coloured state. Colour-change compositions may change colour upon the application of energy for example with a change in temperature or with a change in pressure. Colour-change compositions which change colour with a change in temperature are widely known as thermochromic compositions. Colour-change compositions may also be referred to as colour memory compositions.

In this specification, reference will be made to change between a discoloured and coloured state for convenience but this also encompasses a change between a first coloured state and a second coloured state. Colour-change compositions typically comprise an electron-donating colour-developing organic compound or leuco dye, an electron-accepting compound or colour developer and a compound acting as a reaction medium for reversible electron exchange between the electron-accepting and electron-donating compounds or colour change temperature regulator. The components of the composition are typically micronized or enclosed in microcapsules and may be formulated to produce an ink composition. The composition may be employed in any applications in which temperature dependent colour-change is required or desirable for example in toys, printed materials, decoration, writing instruments, temperature indicators in packaging of medical products such as vaccines and in a wide range of industrial applications such as in curing or bonding processes, pipes, measurement of surface temperature, indication of overheating for example of machinery, plant or the like.

Figure 1:
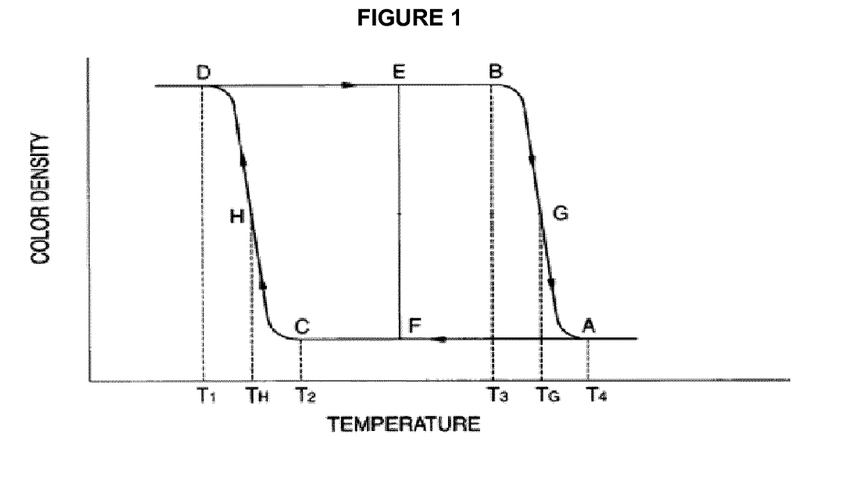
FIG. 1 shows a typical plot of changes in colour density against temperature for thermochromic compositions.

Thermochromic compositions reversibly change colour or change between a coloured and discoloured state when subjected to a change in temperature of a sufficient magnitude. Typically, an increase in temperature will lead to the ink having a discoloured state while cooling will lead to reappearance of colour. As temperature increases, the thermochromic composition will retain colour until the temperature reaches a maximum temperature for retention of the complete coloured state, known as the "maximum colour-retaining temperature" or $T_3$ as shown in FIG. 1 of the accompanying drawings. The composition will then become progressively discoloured as the temperature increases until it reaches a completely discoloured state at a temperature known as the "complete discolouring temperature" or $T_4$, the minimum temperature for achieving the completely discoloured state. The mean temperature between $T_3$ and $T_4$ is known as $T_G$.

As the thermochromic composition cools from a discoloured state, the composition remains discoloured until a temperature is reached below which colour reappears, known as the "minimum discoloured state retaining temperature) or $T_2$ as the temperature decreases, colour reappears fully at a temperature known as the "complete colouring temperature" or $T_1$. The mean temperature between $T_1$ and $T_2$ is referred to as $T_H$. The thermochromic composition has a hysteresis width, known as $\Delta H$ which is the temperature difference between $T_H$ and $T_G$.

As the composition is subject to heating or cooling, the coloured state or discoloured state of the thermochromic composition may be retained after removal of the source of heat or cold required for respectively discoloration or coloration. Depending on whether the composition approaches a particular temperature from a lower or higher temperature, the composition may be coloured or discoloured at that particular temperature.

Where the thermochromic composition is heated above a certain temperature, in the discoloured state, the coloured state may not reappear on cooling the composition until temperature $T_1$ is reached. This may be referred to as the "locking temperature" This provides a means of determining whether the composition has been subjected to the locking temperature which may be beneficial especially in medical applications or other applications where health or safety considerations are important. The hysteresis width, locking temperature and the minimum temperature at which colour reappears are dependent on the components of the composition.

BACKGROUND ART

U.S. Pat. No. 7,494,537 B2 describes thermochromic colouring colour-memory compositions comprising an electron donative colouring organic compound (A), an electron accepting colouring organic compound (B) to form the thermochromic and (C) a reaction medium of formula I, II or III below:

The components of the composition may be selected to achieve a desired colour memory effect and hysteresis width and T4 temperature dependent on the intended use.

There remains a need for Colour-change compositions and especially thermochromic compositions which provide good thermal and chemical stability and a large hysteresis width. We have now found that novel compounds of a certain structure provide an excellent combination of characteristics suitable for use in a colour-change composition including compatibility with a wide range of electron accepting and electron donating components and enabling control of the colour and discolour characteristics of the composition, stability and which may be tailored to provide desired hysteresis characteristics and flexibility in formulating the colour-change composition.

SUMMARY OF THE INVENTION

In a first aspect, the invention provides a compound of formula (I):

wherein:
- $R_1$, and $R_2$ are independently selected from an optionally substituted linear or branched alkyl group, alkenyl group, alkoxy group, aryl group and an alkylene aryl group; preferably having from 5 to 22 or 6 to 22 carbon atoms, preferably $C_{5-22}$ alkyl or $C_{1-12}$ alkylene or aryl, especially $C_9$ to $C_{17}$ alkyl for example $C_6$ alkyl, $C_{10}$ alkyl, $C_{12}$ alkyl, $C_{14}$ alkyl, $C_{16}$ alkyl, $C_{1-4}$ alkylene and phenyl;
- $X_1$ and $X_2$ are independently selected from —OC(O)—, —CO$_2$— and O and preferably $R_1X_1$ and $R_2X_2$ are not —O-alkenyl;
- $R_3$, $R_4$ and $R_5$ are independently selected from hydrogen and an optionally substituted linear or branched hydrocarbyl group, preferably alkyl group, cycloalkyl group, alkenyl group and alkoxy group; especially hydrogen, $C_{1-10}$ alkyl, more preferably hydrogen and $C_{1-4}$ alkyl, for example methyl;
- $R_6$ is selected from hydrogen, halogen $R_3$, —$X_1R_1$, phenyl and preferably when $R_6$ is —$X_1R_1$, $R_1$ is not aryl, alkenyl or an alkylene aryl group; $R_6$ is preferably selected from hydrogen, $C_{1-10}$ alkyl and —CO$_2R_1$, more preferably hydrogen and $C_{1-4}$ alkyl, —CO$_2R_1$;
- $Y_1$, $Y_2$, $Y_3$ and $Y_4$ are independently selected from hydrogen, $R_3$, —OR$_3$ and halogen provided that —OR$_3$ is not —O-alkenyl; more preferably hydrogen and $C_{1-4}$ alkyl, for example methyl;
- a is 0 to 4; preferably 1, b is 0 or 1; x and y are independently 0 or 1 provided that where x and y are 0, a is 0 and b is 1 and $R_6$ is —CO$_2R_1$.

The term "optionally substituted" as employed herein means that the group or moiety may be substituted with one or more substituents but preferably is unsubstituted. If a substituent is present, it may be selected a group containing a heteroatom but is preferably a hydrocarbyl group containing only hydrogen and carbon atoms. Examples of substituents include nitro, chloro, fluoro, bromo, nitrile, hydroxyl, thiol, a carboxylic acid group, a carboxylic ester group, $C_{1-22}$-alkoxy, $C_{1-22}$-alkyl, $C_{1-22}$-alkenyl, $C_{1-14}$ aryl or $C_{1-6}$ alkaryl, amino, amino $C_{1-22}$-alkyl and amino di ($C_{1-22}$-alkyl).

Examples of alkyl groups include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. Examples of alkenyl groups include ethenyl, 2-propenyl, cyclohexenyl, octenyl, iso-octenyl, hexadecenyl, octadecenyl, iso-octadecenyl and docosenyl. Examples of alkoxy groups include methoxy, ethoxy, propoxy, tert-butoxy and n-butoxy.

The term aryl refers to a five or six membered cyclic, 8-10 membered bicyclic or 10-14 membered tricyclic group with aromatic character and includes groups which contain only hydrogen and carbon atoms and also heteroaromatic groups which contain hydrogen, carbon and one or more heteroatoms, for example, N, O or S. Examples of suitable aryl groups include phenyl, pyridinyl and furanyl. Where the term "alkylaryl" is employed herein, the immediately preceding carbon atom range refers to the alkyl substituent only and does not include any aryl carbon atoms. Examples of alkaryl groups include benzyl, phenylethyl and pyridylmethyl. Advantageously the aryl group is a phenyl group.

In preferred embodiments, optional substituents are selected from halogen, for example chlorine, halo alkyl, for example $C_{1-6}$ halo alkyl and $C_{1-4}$ alkoxy, for example methoxy The phenyl moieties of compound (I) may independently be unsubstituted where $Y_1$ $Y_2$ $Y_3$ and $Y_4$ are hydrogen or substituted by one or more groups of $Y_1$, $Y_2$, $Y_3$ and $Y_4$ other than hydrogen. Where x or y are 0, the respective phenyl moieties are suitably unsubstituted.

Each aryl ring of compound (I), preferably phenyl ring, may have 2 or more $Y_1$, $Y_2$, $Y_3$ and $Y_4$ substituents respectively. Where one or more aryl ring has 2 or more substituents, the substituents are suitably selected from hydroxyl and $C_{1-4}$ alkyl, preferably methyl.

In one preferred embodiment, the compound (I) has a formula (II) wherein a, b, x and y are 1:

wherein $Y_1$, $Y_2$, $Y_3$, $Y_4$, $R_1$, $R_2$, $R_3$, $R_4$, $R_5$, $R_6$, $X_1$ and $X_2$ are as defined above.

In a preferred embodiment of compound (II), $R_3$, $R_4$, $R_5$ and $R_6$ are independently selected from hydrogen and an optionally substituted linear or branched alkyl group, alkenyl group and alkoxy group having from 5 to 22 carbon atoms and are more preferably independently selected from hydrogen and $C_{1-10}$ alkyl, especially and $C_{1-4}$ alkyl and hydrogen. In an especially preferred embodiment and $R_3$, $R_4$, $R_5$ and $R_6$ are independently selected from hydrogen and methyl and desirably are all methyl. The moieties —CR$_3R_4$— and —CR$_5R_6$— may be in an ortho, meta or para relationship to each other, preferably para or meta. Suitably, the moieties —CR$_3R_4$— and $R_1X_1$— and the moieties —CR$_5R_6$ and $R_2X_2$— respectively may be in an ortho, meta or para relationship to each other, preferably para.

Preferably compound (II) has the following formula compound (III):

Compound (III)

in which $Y_1$, $Y_2$, $Y_3$ and $Y_4$ are all hydrogen, and in which $R_1CO_2$— and —$O_2CR_2$ are both in a para position and the two —$C(CH_3)_2$— moieties are in a para or meta relationship as shown in formulae (IV) and (V) below. Preferably $R_1$ and $R_2$ are independently selected from $C_9$ to $C_{15}$ alkyl for example $C_{10}$ alkyl.

Compound (IV)

Compound (V)

Preferably the compounds of formula (IV) are selected from compounds of formulae (IVa), (IVb) and (IVc) as shown below:

(IVa)

(IVb)

(IVc)

The compounds of formula (I) to (V) as defined above and in particular of formulae (IVa), (IVb) and (IVc) are particularly useful as components of a colour change, preferably thermochromic, composition. The invention provides for use of a compound of any one of formulae (I) to (V) as defined above and in particular of formulae (IVa), (IVb) and (IVc) in a colour-change composition, preferably thermochromic composition.

The invention provides in a second aspect a colour change, preferably thermochromic, composition comprising: A) an electron donating organic colouring compound, B) an electron accepting compound and C) a compound of formula (I) as defined above In preferred embodiments of the second invention, the compound (I) is suitably a compound selected from a compound of formulae (II) to (V) defined above and in particular of formulae (IVa), (IVb) and (IVc) defined above.

Compositions and pigments according to the invention provide a wide hysteresis and a tuneable hysteresis. By varying the colour-change composition formulation the width of the hysteresis may be varied and the complete decolouring temperature T4 may be varied, allowing excellent flexibility in the design of the colour-change microcapsule pigment.

Any suitable known or future electron donating colouring compounds, component A) of the composition and conventionally known as a colour former, may be employed. Examples of suitable classes of compounds include indolyles, phthalides, azaphthalides, fluorans, styrylquinoline and diazarhodamine lactones.

Particular examples of component A) include 2'-chloro-6'-diethylaminofluoran, 6'-(diethylamino)-2'-(phenylamino)-3H-spiro[2-benzofuran-1,9'-xanthen]-3-one, 3-(4-diethylamino-2-hexyloxyphenyl)-3-(1-ethyl-2-methylindol-3-yl)-4-azaphthalide, 3,3-bis(p-dimethylaminophenyl)-6-dimethylaminophthalide, 3-(4-diethylaminophenyl)-3-(1-ethyl-2-methylindol-3-yl)phthalide, 3,3-bis(1-n-butyl-2-methylindol-3-yl)phthalide, 3,3-bis(2-ethoxy-4-diethylaminophenyl)-4-azaphthalide, 3-[2-ethoxy-4-(N-ethylanilino)phenyl]-3-(1-ethyl-2-methylindol-3-yl)-4-azaphthalide, 3,6-diphenylaminofluoran, 3,6-dimethoxyfluoran, 3,6-di-n-butoxyfluoran, 2-methyl-6-(N-ethyl-N-p-tolylamino)fluoran, 3-chloro-6-cyclohexylaminofluoran, 2-methyl-6-cyclohexylaminofluoran, 2-(2-chloroanilino)-6-di-n-butylaminofluoran, 2-(3-trifluoromethylanilino)-6-diethylaminofluoran, 2-(N-methylanilino)-6-(N-ethyl-N-p-tolylamino)fluoran, 1,3-dimethyl-6-diethylaminofluoran, 2-chloro-3-methyl-6-diethylaminofluoran, 2-anilino-3-methyl-6-diethylaminofluoran, 2-anilino-3-methyl-6-di-n-butylaminofluoran, 2-xylidino-3-methyl-6-diethylaminofluoran, 1-2-benz-6-diethylaminofluoran, 1,2-benz-6-(N-ethyl-N-isobutylamino)fluoran, 1,2-benz-6-(N-ethyl-N-isoamylamino)fluoran, 2-(3-methoxy-4-dodecoxystyryl)quinoline, spiro[5H-(1)benzopyrano(2,3-d)pyrimidine-5,1'(3'H)isobenzofuran]-3'-one, 2-(diethylamino)-8-(diethylamino)-4-methyl-, spiro[5H-(1)benzopyrano(2,3-d)pyrimidine-5,1'(3'H)isobenzofuran]-3'-one, 2-(di-n-butylamino)-8-(di-n-butylamino)-4-methyl-, spiro[5H-(1)benzopyrano(2,3-d)pyrimidine-5,1'(3'H)isobenzofuran]-3'-one, 2-(di-n-butylamino)-8-(diethylamino)-4-methyl-, spiro[5H-(1)benzopyrano(2,3-d)pyrimidine-5,1'(3'H)isobenzofuran]-3'-one, 2-(di-n-butylamino)-8-(N-ethyl-N-i-amylamino)-4-methyl-, spiro[5H-(1)benzopyrano(2,3-d)pyrimidine-5,1'(3'H)isobenzofuran]-3'-one, 2-(di-n-butylamino)-8-(din-butylamino)-4-phenyl, 3-(2-methoxy-4-dimethylaminophenyl)-3-(1-butyl-2-methylindol-3-yl)-4,5,6,7-tetrachlorophthalide, 3-(2-ethoxy-4-diethylaminophenyl)-3-(1-ethyl-2-methylindol-3-yl)-4,5,6,7-tetrachlorophthalide, and 3-(2-ethoxy-4-diethylaminophenyl)-3-(1-pentyl-2-methylindol-3-yl)-4,5,6,7-tetrachlorophthalide.

Advantageously, component A) is selected from the group consisting of 3-(4-diethylamino-2-hexyloxyphenyl)-3-(1-ethyl-2-methylindol-3-yl)-4-azaphthalide, 2'-chloro-6'-diethylaminofluoran, 6'-(diethylamino)-2'-(phenylamino)-3H-spiro[2-benzofuran-1,9'-xanthen]-3-one, 3,3-bis(1-n-butyl-2-methylindol-3-yl)phthalide and 2-(2-chloroanilino)-6-di-n-butylaminofluoran.

Any suitable known or future electron accepting group component B) of the composition may be employed. Examples of suitable classes of compounds include compounds having labile or active protons, pseudo-acidic compounds, or electron voids. Examples of classes of compounds having active protons include compounds having a phenolic group such as mono- and poly-phenols bearing substituents known in the art and their metal salts.

Examples of suitable component B) compounds include:
phenol, o-cresol, tertiary butyl catechol, nonylphenol, n-octylphenol, n-dodecylphenol, n-stearylphenol, p-chlorophenol, p-bromophenol, o-phenylphenol, 4,4'-cyclohexylidenebisphenol, n-butyl p-hydroxybenzoate, n-octyl p-hydroxybenzoate, resorcin, dodecyl gallate, 2,2-bis(4-hydroxyphenyl)propane, 4,4-dihydroxydiphenylsulfone, 1,1-bis(4-hydroxyphenyl) ethane, 2,2-bis(4-hydroxy-3-methylphenyl)propane, bis(4-hydroxyphenyl) sulfide, 1-phenyl-1,1,-bis(4-hydroxyphenyl)ethane, 1,1-bis(4-hydroxyphenyl)-3-methylbutane, 1,1-bis(4-hydroxyphenyl)-2-methylpropane, 1,1-bis(4-hydroxyphenyl)-n-hexane, 1,1-bis(4-hydroxyphenyl)-n-heptane, 1,1-bis(4-hydroxyphenyl)-n-octane, 1,1-bis(4-hydroxyphenyl)-n-nonane, 1,1-bis(4-hydroxyphenyl)-n-decane, 1,1-bis(4-hydroxyphenyl)-n-dodecane, 2,2-bis(4-hydroxyphenyl)butane, 2,2-bis(4-hydroxyphenyl)ethyl propionate, 2,2-bis(4-hydroxyphenyl)-4-methylpentane, 2,2-bis(4-hydroxyphenyl) hexafluoropropane, 2,2-bis(4-hydroxyphenyl)-n-heptane, 2,2-bis(4-hydroxyphenyl)-n-nonane, 4,4',4"-methylidenetrisphenol, 2,6-bis[(2-hydroxy-5-methylphenol)methyl]-4-methylphenol, 4,4'-[1-[4-[1-(4-hydroxyphenyl)-1-methylethyl]phenyl]ethylidene]bisphenol, 4,4',4"-methylidenetris[2-methylphenol], 4,4'-[(2-hydroxyphenyl)methylene]bis[2,3,6-triphenylphenol], 2,2-methylenebis[6-[(2-hydroxy-5-methylphenyl)methyl]-4-methylphenol], 2,4,6-tris(4-hydroxyphenylmethyl)1,3-benzenediol, 4,4',4"-ethylidenetrisphenol, 4,4'-[(4-hydroxyphenyl)methylene]bis[2-methylphenol], 4,4-[(4-hydroxyphenyl)methylene]bis[2,6-dimethylphenol], 4,4'-[(4-hydroxyphenyl)methylene]bis[2-methylphenol], 4,4'-[(4-hydroxyphenyl)methylene]bis[2,6-dimethylphenol], 4,4'-[(4-hydroxy-3-methoxyphenyl)methylene]bis[2,6-dimethylphenol], 2,4-bis[(5-methyl-2-hydroxyphenyl)methyl]-6-cyclohexylphenol, 4,4'-[1-[4-[1-(4-hydroxy-3-methylphenol)-1-methylethyl]phenyl]ethylidene]bis[2-methylphenol], 4,4'-[(4-hydroxyphenyl)methylene]bis[2-cyclohexyl-5-methylphenol], 4,6-bis[(4-hydroxyphenyl)methyl]1,3-benzenediol, 4,4'-[(3,4-dihydroxyphenyl)methylene]bis[2,6-dimethylphenol], 4,4'-(1-phenylethylidene)bisphenol, 5,5'-(1-methylethylidene)bis[1-phenyl-2-ol], 4,4',4"-methylidenetrisphenol, 4,4'-[1-[4-[1-(4-hydroxyphenyl)-1-methylethyl]phenyl]ethylidene]bisphenol, 4,4'-(phenylmethylene)bisphenol, 4,4'-[1,4-phenylenebis(1-methylethylidene)]bis[2-methylphenol], 5,5'-(1,1-cyclohexylidene)bis[1-biphenyl-2-ol], bis(3-methyl-4-hydroxyphenyl)sulfide, bis(3,5-dimethyl-4-hydroxyphenyl), bis(3-ethyl-4-hydroxyphenyl)sulfide, bis(3,5-diethyl-4-hydroxyphenyl)sulfide, bis(3-propyl-4-hydroxyphenyl)sulfide, bis(3,5-dipropyl-4-hydroxyphenyl) sulfide, bis(3-t-butyl-4-hydroxyphenyl)sulfide, bis(3,5-t-butyl-4-hydroxyphenyl)sulfide, bis(3-pentyl-4-hydroxyphenyl)sulfide, bis(3-hexyl-4-hydroxyphenyl) sulfide, bis(3-heptyl-4-hydroxyphenyl)sulfide and bis(5-octyl-2-hydroxyphenyl)sulfide.

Advantageously component B) can be a mixture of at least two of the above-mentioned component. Advantageously component B) is selected from the group consisting of 2,2-bis(4'-hydroxyphenyl)hexafluoropropane, 1,1-bis(4'-hydroxyphenyl)-2-methylpropane and mixture thereof, more advantageously it is a mixture of 2,2-bis(4'-hydroxyphenyl)hexafluoropropane and 1,1-bis(4'-hydroxyphenyl)-2-methylpropane Suitably, the ratio of components B) to C) In parts by weights is in the range 0.5 to 40 and preferably within 1 to 20. The ratio of components A) to C) In parts by weights is suitably in the range 0.5 to 30 and preferably within 1 to 20.

Each component may comprise 2 or more components. Conventional additives for example emulsifiers, antioxidants, UV absorbers, metal chelates may also be included in the composition.

We have found that by including a non-ionic surfactant in the composition, improved stability against colour change when the composition is subjected to pressure in the clear state may be secured.

The invention provides in a further aspect for the use of a non-ionic surfactant in a colour-change composition or a colour change microencapsulated pigment, preferably according to the invention, which has a coloured state and a clear state to provide increased stability or resistance to colour-change when subjected to pressure, particularly when the composition is in a clear or colourless state.

The term "surfactant" refers to a compound which has a hydrophilic group or region and a hydrophobic group or region. The non-ionic surfactant is preferably an alkoxylate which has a hydrophobic terminal group.

The hydrophobic terminal group is suitably a hydrocarbyl and preferably an alkyl, group. The alkyl group is preferably a $C_1$ to $C_{22}$ group, more preferably $C_7$ to $C_{22}$ especially a $C_9$ to $C_{15}$ group for example a mixed $C_9/C_{11}$ group and a mixed $C_{13}/C_{15}$ group. The alkyl group is suitably derived from an alcohol or an amine, preferably a primary amine.

The alkoxylate is suitably based on multiple units of alkylene oxide and is preferably an ethoxylate, a propoxylate, a butoxylate or a mixture of two or more alkoxylates. Preferably the alkoxylate is an ethoxylate. The mixture may be a random or block arrangement of the different alkoxylates. The alkoxylate preferably comprises from 2 to 30, more preferably 2 to 15 and desirably 3 to 12 alkylene oxide units.

Suitably the non-ionic surfactant has a formula Q:

wherein R' is a hydrocarboyl, for example an alkyl group, alkenyl group, aryl group and alkylaryl group having from 1 to 22 carbon atoms, more preferably a $C_1$ to $C_{22}$ group, more preferably a $C_7$ to $C_{22}$ and especially a $C_9$ to $C_{15}$ alkyl, alkenyl or alkylaryl group; Het is O, S or NH or NR'; g is 2 to 4, preferably 2; r is 2 to 30, preferably 3 to 12; and R" is selected independently from R' and H.

The non-ionic surfactant may be "end-capped" which refers to the case where R" is selected from the substituents defining R'. The terminal groups R' and R" may be the same or different.

Suitably, the non-ionic surfactant has a molecular weight from 300 to 1500, preferably 500 to 1000. Preferably the non-ionic surfactant comprises an alcohol alkoxylate. Examples of suitable non-ionic surfactants include those available under the BIOSOFT trade name from Stepan, the LUTENSOL trade name from BASF, the EMULSOGEN and GENAPOL trade names from Clariant and products available under the EMPILAN, HYDRAPOL, SURFONIC, BIONIC and TERIC trade names from Huntsman FIG. 1 of the accompanying drawings shows a typical hysteresis profile for a reversible colour-change composition. Colour density is plotted against temperature. The colour density advancement due to temperature change on heating and cooling cycles is illustrated and progresses in the direction of the arrow. Point A at T4 is the fully decolourised state (herein will be called fully decolorized temperature); point B at T3 is the point at which the composition is in a fully coloured state during heating. Point C shows the last point at which the composition is fully discoloured during cooling at T2; Point D is the point at which the composition is in a fully coloured state during cooling at T1 (herein will be called fully coloured temperature). It will be apparent that the thermochromic composition may be in a fully coloured state or a fully discoloured state at a said temperature between T2 and T3 depending on whether the composition is being heated from a lower temperature or cooled form a higher temperature. The difference between temperatures T3 and T2 ($\Delta H_{T3-T2}$) is the practical value for hysteresis (herein will be called practical hysteresis).

The difference between T1 and T2 ($\Delta H_{T2-T1}$) is related to the sensitivity of the colour change mechanism. The lower the value of $\Delta H_{T2-T1}$, the sharper the transition between the last point of the fully coloured state and the fully discoloured state and also the sharper the transition between last point of the fully discoloured state and the fully coloured state. Colour density difference or colour contrast is measured by the difference of colour between E and F as shown in FIG. 1.

The components A), B) and C) of the composition may be selected and the relative amounts employed to tailor properties of the composition to the desired use. The component is suitably selected to provide the desired practical hysteresis and the sensitivity of the colour change, as well as the temperature T1 and T4.

Suitably, the practical hysteresis range may be from 10 to 80° C. and preferably is at least 50° C. The fully coloured temperature T4 is suitably higher than ambient temperature, preferably higher than 50° C. The fully decolorized temperature T1 is suitably lower than 20° C., preferably lower than 0° C.

The composition of the invention suitably comprises a homogeneous solubilised mixture of the components A), B) and C) of the composition. Preferably, components A) and B) are dissolved in component C) to produce the composition.

Component C is suitably synthesised by stirring a mixture of 1 mole of bisphenol (biphenol) and 2.5 moles of triethyl amine in acetone and cooling to 5° C. 2.2 moles of acid chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. Suitably, the relative quantities of bisphenol (biphenol)/acid chloride/triethylamine are 1/2.2/2.5 moles. Bisphenols are available from Mitsui Chemical. Biphenol is available from Chemos (Germany). Bisphenol P and bisphenol M are available from Mitsui Chemical,

US 2010/075253 describes phenol-based compounds that may be employed in the synthesis of Bisphenol P and Bisphenol M and analogues thereof.

Bisphenol P may be produced by reacting:

or an analogue thereof with phenol for example as set out in Stetson, Christopher M.; Nishikawa, Shiro; Purkiss, David W.; Dalley; Bartsch, Richard A. Journal of Physical Organic Chemistry, 2005, vol. 18, #11 p. 1107-1115 or as described in Hung; Werbel European Journal of Medicinal Chemistry, 1983, vol. 18, #1 p. 61-66. For analogues, with other substituents, a corresponding aromatic compound may be employed.

The synthesis of Bisphenol M is described in U.S. Pat. No. 6,326,522 B1. WO2015/033750 describes compounds of formula:

(I)

in which R1 and R2 independently have 7 to 21 carbon atoms and R3 is hydrogen or an alkyl group having 1 to 7 carbon atoms.

U.S. Pat. Nos. 3,979,462 and 6,992,166 describe the synthesis of compounds of the general formula below:

(I)

in which Ar represents an aromatic group having 6 to 20 carbon atoms, $R_1$ to $R_4$ independently represent hydrogen, an alkyl group having 1 to 20 carbon atoms, a cycloalkyl group having 5 to 20 carbon atoms or an aralkyl group having 7 to 20 carbon atoms in which $R_1$ and $R_3$ do not simultaneously represent hydrogen and $R_2$ and $R_4$ do not simultaneously represent hydrogen.

Suitably, the colour-change composition is microencapsulated to provide a colour-change microcapsule pigment by a known method.

The invention further provides a colour-change microencapsulated pigment comprising a composition according to the invention which is microencapsulated. Suitably, the composition is homogeneous. Preferably the composition comprises components A), B), C) and a non-ionic surfactant to provide improved stability or resistance to colour-change in the clear state as described above.

The microcapsules suitably have a particle size from 0.5 to 50 microns, preferably 1 to 20 microns so as to provide suitable dispersion stability and processing characteristics whilst providing high density colour.

Unless otherwise stated, all particle sizes referred to herein are measured by volume using a Coulter particle size analyser by laser diffraction, All figures given for particle size represents the 90% fraction of particles showing diameter no larger than the specified size.

The composition may be microencapsulated by any known method, for example by using isocyanate interfacial polymerisation, melamine or urea formaldehyde interfacial polymerisation, free radical interfacial polymerisation, polycondensation of epoxy or complex coacervation.

Microencapsulation allows the colour-change composition to retain its composition when in contact with chemicals or heat. Chemicals are blocked by the microcapsule walls and the formulation of the composition is retained. The microencapsulation may also have a practical benefit on the way the colour-change composition performs.

The microencapsulated pigment enables the colour-change colour memory composition to be used in paint, coating and plastic vehicle either as water based pigment dispersion or a pigment powder. The composition or microencapsulated pigment may be employed in any applications in which temperature dependent colour-change is required or desirable for example in toys, printed materials, decoration, writing instruments, temperature indicators in packaging of medical products such as vaccines and in a wide range of industrial applications such as in curing or bonding processes, pipes, measurement of surface temperature, indication of overheating for example of machinery, plant or the like.

As further examples, the compositions and pigments of the present invention may be employed in inks for multiple printing mode offset, flexo, gravure, screen, 3D printing, pad printing, spray coating and other coating modes and ink jet. The compositions and pigments may be provided as an ink composition for use in writing implements such as ball point pen, marking pen, fountain pen, gel pen, roller ball pen and other inks vehicles.

In a further aspect of the invention, there is provided an ink composition for a writing implement which comprises a colour-change microencapsulated pigment according to the invention.

Advantageously, the ink composition may contain also a carrier, such as a solvent for example an aqueous or organic solvent, advantageously an aqueous solvent. The ink composition may also contain other additives known to one skilled in the art to be useful for preparing an ink composition for example a dispersing agent, an emulsifying agent, a surface-tension modifier, a surfactant, an humectant, a resin, a biocide and the like.

The invention further provides a writing implement comprising a writing implement containing an ink composition according to the invention.

In particular the writing implement may be a ball point pen, a marking pen, a fountain pen, a gel pen or a roller ball pen.

Advantageously the writing implement contains a means for erasing the ink composition.

In a further aspect, the invention provides in combination, a writing implement adapted to receive an ink composition according to the invention and an ink composition for charging to the writing implement.

The colour-change composition or pigment may be used in vehicles such as wax, polymer resins, thermosetting resins where the melt blending of the colour-change colour memory pigment allows manufacturing of pellet, powder of moulded or injected articles such as toys.

The present memory colour-change composition pigment can give memory colour change property to a variety of different substrates and materials: gel, inks, paper, synthetic paper, coated paper, fiber, plastics, glass metal ceramic, wood, stone, plastics, concrete, synthetic glass.

Colour-change compositions of the invention are especially useful in the production of printing inks for preparation of labels to provide a temperature indicator. Prior art with conventional colour-change compositions typically indicate when a particular temperature is reached without any further indication.

A colour-change composition or pigment of this invention provides an indication of when temperature T4 is exceeded by remaining colourless, until the composition is subjected to temperature T1 and regaining colour at this point.

The invention provides a colour-change composition or pigment where component C) is such that the composition or pigment temperature has a T2 temperature at a first temperature, for example 0° C. and a T3 temperature above a second temperature, for example 50° C.

A composition with these characteristics allows the design of an indicator which provides an indication of whether the indicator has been subjected to a particular temperature.

The invention further provides an indicator comprising a first portion of a colour-change composition in its coloured state and a second portion of the same colour-change composition in its discoloured state wherein the composition is according to the present invention.

Suitably, the indicator is printed with a memory composition pigment, preferably converted into printed ink, heated to temperature exceeding temperature T4 prior to the printing process. A second sample of the composition is then suitably cooled to below temperature T1 and printed on the indicator, suitably next to the first print of the thermochromic composition. The printed label is allowed to dry at temperature not exceeding temperature T3 and not below temperature T2.

In a further aspect, the invention provides a process for producing an indicator comprising providing a support with a first portion of the colour-change composition, pigment or ink having colour change temperatures T1, T2, T3 and T4, heating the first portion of the colour-change composition, pigment or ink to a temperature exceeding T4, cooling a second portion of the colour-change composition, pigment or ink composition to a temperature below T1, applying the said second portion to the support and drying the colour-change composition, pigment or ink composition at temperature not exceeding temperature T3 and not below temperature T2.

The colour-change composition is preferably a thermochromic composition.

The combination on the label is now suitable for indication of temperature below T2. By tuning the temperature T2 to 0° C., the indicator may be employed to provide a visual or readable indication of when the indicator and any article or material to which it is applied has been subjected to a temperature of less than 0° C. In this way, the indicator may act as a "freeze indicator".

Figure 2A:
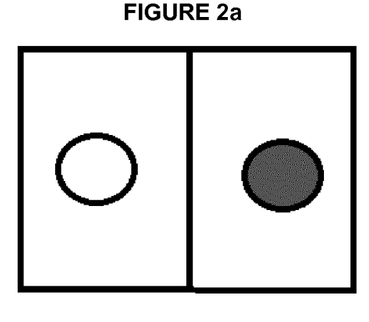
FIGS. 2a to 2c show a temperature freezing indicator label according to the invention based on a memory composition according to the invention.
Figure 2B:
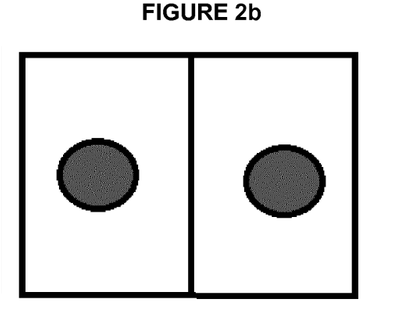
Figure 2C:
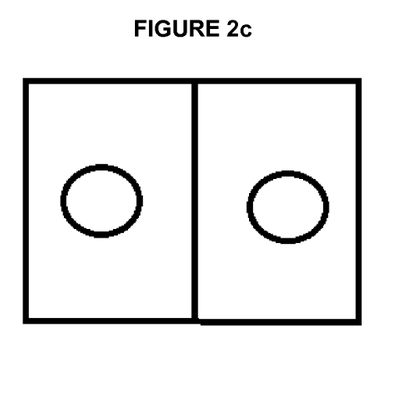

By way of illustration, in the initial state at ambient temperature above T2 and below T3 is represented in FIG. 2a. As the temperature drops below the temperature T2, and is kept below T4 at all times, the state of the indicator changes to that shown in FIG. 2b. By raising the temperature to greater than T3 the indicator provides two colourless compositions as shown in FIG. 2c).

The indicator may also be configured so it may not be reset and provides a single use indicator.

The invention provides for a single use indicator comprising a first portion of a colour-change composition in its coloured state and a second portion of the same colour-change composition in its discoloured state wherein the composition is according to the present invention.

Suitably, the indicator has a thermochromic composition or pigment according to the invention suitably in the form of a printable ink applied to it and heated to a temperature exceeding T4 prior to application to the indicator, for example in a printing process. An ink showing permanent colour change at a desired temperature, for example 50° C. is applied to the indicator, for example printed next to the memory composition pigment converted into printed ink. Any known permanent colour change ink may be employed and a preferred example is available from TMC Hallcrest, under the brand name Kromagen. The printed label is allowed to dry at temperature not exceeding T3 or 50° C. and preferably not below $T_2$. The combination on the label is now suitable for indication of temperature below zero, of what can be cold a "freeze indicator". The indicator used a single time.

Figure 3A:
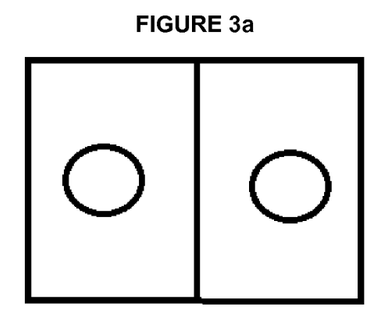
FIGS. 3a to 3c show examples of a temperature indicator label according to the invention based on a memory composition containing Kromagen ink according to the invention.
Figure 3B:
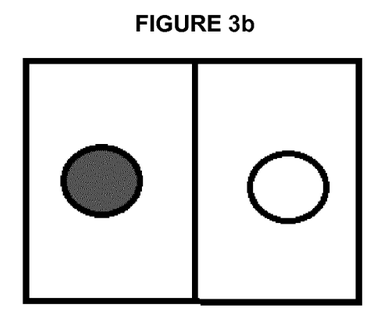
Figure 3C:
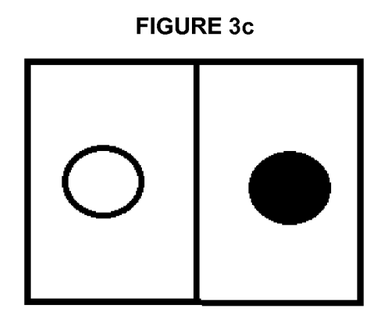

By way of illustration, FIGS. 3a, 3b and 3c illustrate the various forms of the indicator where the indicator comprises a composition according to the invention comprising Kromagen ink. FIG. 3a shows the initial state at ambient temperature above T2 and below the temperature of colour transition of Kromagen. FIG. 3b shows the indicator as the temperature drops below T2 and below the temperature at which Kromagen changes colour and FIG. 3c shows the indicator as it appears after heating above T4.

The invention is now illustrated by the following non-limiting examples in which parts are by weight unless otherwise stated.

EXAMPLE 1

A thermochromic colour memory composition was obtained by homogeneously compatibilizing:

4 parts of 3-(4-diethylamino-2-hexyloxyphenyl)-3-(1-ethyl-2-methylindol-3-yl)-4-azaphthalide (component A)) available from Yamada Chemicals and 6 parts 2,2-bis(4'-hydroxyphenyl)hexafluoropropane and 6 parts of 1,1-bis(4'-hydroxyphenyl)-2-methylpropane (both components B)) available from Sigma Aldrich and 84 parts of 4,4'-[1,4-Phenylenebis(1-methylethylydene)]bis(4-phenyldecanoate) (Component C, specifically component IVa) as shown below):

Component IVa is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of decanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 2

A thermochromic colour memory composition was obtained by homogeneously compatibilizing:

4 parts of 3,3-bis(1-n-butyl-2-methylindol-3-yl)phthalide (Component A)) available from Yamamoto Chemicals and 6 parts 2,2-bis(4'-hydroxyphenyl)hexafluoropropane and 6 parts of 1,1-bis(4'-hydroxyphenyl)-2-methylpropane (both Component B)) available from Sigma Aldrich and 84 parts of 4,4'-[1,4-Phenylenebis(1-methylethylydene)]bis(4-phenyldodecanoate) (Component C) specifically component IVb) as shown below):

Component IVb was prepared using the same procedure as described in Example 1 for Component IVa save that dodecanoyl chloride was employed rather than decanoyl chloride.

The resulting memory composition changed colour from magenta to colourless. The thermochromic colour memory composition was heated above T4. 100 parts of the hot thermochromic colour memory composition was then dis- persed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

The resulting dispersion was then drum dried and the pigment was isolated in encapsulated form, the thermochromic colour memory pigment having a particle size of 2.5 microns changed colour from magenta to colourless.

EXAMPLE 3

A thermochromic colour memory composition was obtained by homogeneously compatibilizing:

4 parts of 2-(2-chloroanilino)-6-di-n-butylaminofluoran (Component A)) available from Hodogaya Chemical Co. Ltd. and 6 parts 2,2-bis(4'-hydroxyphenyl)hexafluoropropane and 6 parts of 1,1-bis(4'-hydroxyphenyl)-2-methylpropane (Component B)) available from Sigma Aldrich and 84 parts of 4,4'-[1,4-Phenylenebis(1-methylethylydene)]bis(4-phenylhexadecanoate) (Component C) specifically component IVc) as shown below). The resulting memory composition changed colour from black to colourless.

Component IVc was prepared using the same procedure as described in Example 1 for Component IVa save that hexadecanoyl chloride was employed rather than decanoyl chloride.

The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

The resulting dispersion was then air dried and the pigment was isolated in encapsulated form, the thermochromic colour memory pigment having a particle size of 4 microns changed colour from black to colourless.

EXAMPLE 4

A thermochromic colour memory composition was obtained by homogeneously compatibilizing:

4.1 parts of 3-Diethylamino-6-methyl-7-(2,4-xylidino) fluoran (component A) available from Yamamoto Chemicals and 4.75 parts 4,4'-Cyclohexylidenebisphenol and 4.75 parts of 4-Hydroxyphenyl-4'-isopropoxyphenyl sulfone (both components B) available from Sigma Aldrich and 86.4 parts of 4,4'-[1,4-Phenylenebis(1-methylethylydene)]bis(4-phenyldecanoate) (Component C, specifically component IVa) as shown below):

Component IVa is synthesised as per example 1

The resulting memory composition changed colour from black to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

EXAMPLE 5

A thermochromic colour memory composition was obtained by homogeneously compatibilizing:

4.1 parts of 3,3-Bis(1-butyl-2-methylindol-3-yl)phthalide (component A) available from Yamamoto Chemicals and 5.3 parts 4,4'-Cyclohexylidenebisphenol and 4.1 parts of 4,4'-(1-Phenylethylidene)bisphenol (both components B)) available from Sigma Aldrich and 86.5 parts of 4,4'-[1,4-Phenylenebis(1-methylethylydene)]bis(4-phenyldecanoate) (Component C, specifically component IVa) as shown below):

Component IVa is synthesised as per example 1

The resulting memory composition changed colour from magenta to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

EXAMPLE 6

A thermochromic colour memory composition was obtained by homogeneously compatibilizing:

4.1 parts of 3,3-bis(2-ethoxy-4-diethylaminophenyl)-4-azaphthalide (component A) available from Yamamoto Chemicals and 3 parts 4,4'-Cyclohexylidenebisphenol, 6.5 parts of 4,4'-(1-Phenylethylidene)bisphenol, 2 parts of 4,4'-Thiodiphenol and 2 parts of 2-hydroxy-4-methoxy benzophenone (all components B)) available from Sigma Aldrich and 82.4 parts of 4,4'-[1,4-Phenylenebis(1-methylethylydene)]bis(4-phenyldecanoate) (Component C, specifically component IVa) as shown below):

Component IVa is synthesised as per example 1

The resulting memory composition changed colour from turquoise to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

EXAMPLE 7

A thermochromic colour memory composition was obtained by homogeneously compatibilizing:

7 parts 2'-chloro-6'-diethylaminofluoran (component A) available from Yamamoto Chemicals and 6 parts 4,4'-Cyclohexylidenebisphenol, 6 parts of 4,4'-(1-Phenylethylidene)bisphenol, 4 parts of 4,4'-Thiodiphenol and 2 parts of 2-hydroxy-4-methoxy benzophenone (all components B)) available from Sigma Aldrich and 75 parts of 4,4'-[1,4-Phenylenebis(1-methylethylydene)]bis(4-phenyldecanoate) (Component C, specifically component IVa) as shown below):

Component IVa is synthesised as per example 1

The resulting memory composition changed colour from red to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

EXAMPLE 8

A thermochromic colour memory composition was obtained by homogeneously compatibilizing:

3.1 parts of 6'-(diethylamino)-2'-(phenylamino)-3H-spiro [2-benzofuran-1,9'-xanthen]-3-one (component A) and 5.1 parts 4,4'-Cyclohexylidenebisphenol, 5.1 parts of 4,4'-(1-Phenylethylidene)bisphenol and 1.9 parts of 2-hydroxy-4-methoxy benzophenone (all components B) available from Sigma Aldrich and 84.8 parts of 4,4'-[1,4-Phenylenebis(1-methylethylydene)]bis(4-phenyldecanoate) (Component C, specifically component IVa) as shown below):

Component IVa is synthesised as per example 1

The resulting memory composition changed colour from green to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

EXAMPLE 9

A thermochromic colour memory composition was obtained by homogeneously compatibilizing:

3 parts of 3-(4-diethylamino-2-hexyloxyphenyl)-3-(1-ethyl-2-methylindol-3-yl)-4-azaphthalide (component A) available from Yamada Chemicals and 12.6 parts 4,4'-Isopropylidenedi-o-cresol available from Sigma Aldrich (components B) and 84.4 parts of 4,4'-[1,4-Phenylenebis(1-methylethylydene)]bis(4-phenylundecanoate) (Component C, specifically component IVd) as shown below):

Component IVd is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of undecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 10

A thermochromic colour memory composition was obtained by homogeneously compatibilizing:

4 parts of 3-(4-diethylamino-2-hexyloxyphenyl)-3-(1-ethyl-2-methylindol-3-yl)-4-azaphthalide (component A)) available from Yamada Chemicals, 6.4 parts 2,2-bis(4'-hydroxyphenyl)hexafluoropropane and 6.4 parts of butyl 4-hydroxybenzoate available from Sigma Aldrich (both components B) and 83.2 parts of 4,4'-[1,4-Phenylenebis(1-methylethylydene)]bis(4-phenyltetradecanoate) (Component C, specifically component IVe) as shown below):

Component IVe is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of tetradecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 11

A thermochromic colour memory composition was obtained by homogeneously compatibilizing:

4.1 parts of 3-(4-diethylamino-2-hexyloxyphenyl)-3-(1-ethyl-2-methylindol-3-yl)-4-azaphthalide (component A) available from Yamada Chemicals, 4.85 parts 2,2-bis(4'-hydroxyphenyl)hexafluoropropane, 4.85 parts 4,4'-(1-Phenylethylidene)bisphenol and 8.6 parts of lauric acid (all components B) available from Sigma Aldrich and 77.6 parts of 4,4'-[1,4-Phenylenebis(1-methylethylydene)]bis(4-phenylhexanoate) (Component C, specifically component IVf) as shown below):

Component IVf is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of hexanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 12

A thermochromic colour memory composition was obtained by homogeneously compatibilizing:

4.15 parts of 3-(4-diethylamino-2-hexyloxyphenyl)-3-(1-ethyl-2-methylindol-3-yl)-4-azaphthalide (component A)) available from Yamada Chemicals and 4.85 parts 2,2-bis(4'-hydroxyphenyl)hexafluoropropane and 4.85 parts of 1,1-bis (4'-hydroxyphenyl)-2-methylpropane (both components B)) available from Sigma Aldrich and and 86.15 parts of 4,4'-[1,3-Phenylenebis(1-methylethylydene)]bis(4-phenylhexadecanoate) (Component C, specifically component Va) as shown below):

Component Va is suitably synthesised by stirring a mixture of 1 mole of 4,4'-(1,3-Phenylenediisopropylidene)bisphenol, commercially available from Mitsui Chemicals, and 2.5 moles of triethyl amine in acetone and cooling to 5° C. 2.2 moles of hexadecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 13

A thermochromic colour memory composition was obtained by homogeneously compatibilizing:

4.1 parts of 3-(4-diethylamino-2-hexyloxyphenyl)-3-(1-ethyl-2-methylindol-3-yl)-4-azaphthalide (component A) available from Yamada Chemicals, 4.85 parts 4,4'-(1-Phenylethylidene)bisphenol and 4.85 parts 4,4'-Isopropylidenedi-o-cresol available from Sigma Aldrich (both components B) and 86.2 parts of 4,4'-[1,3-Phenylenebis(1-methylethylydene)]bis(4-phenyltetradecanoateanoate) (Component C, specifically component Vb) as shown below):

Component Va is suitably synthesised by stirring a mixture of 1 mole of 4,4'-(1,3-Phenylenediisopropylidene)bisphenol, commercially available from Mitsui Chemicals, and 2.5 moles of triethyl amine in acetone and cooling to 5° C. 2.2 moles of tetradecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

EXAMPLE 14

A thermochromic colour memory composition was obtained by homogeneously compatibilizing:

3.1 parts of 6'-(diethylamino)-2'-(phenylamino)-3H-spiro[2-benzofuran-1,9'-xanthen]-3-one (component A) and 5.1 parts 4,4'-Cyclohexylidenebisphenol, 5.1 parts of 4,4'-(1-Phenylethylidene)bisphenol and 1.9 parts of 2-hydroxy-4-methoxy benzophenone (all components B) available from Sigma Aldrich and 70 parts of 4,4'-[1,4-Phenylenebis(1-methylethylydene)]bis(4-phenyldecanoate) and 14.8 parts of 4,4'-[1,4-Phenylenebis(1-methylethylydene)]bis(4-phenyloctanoate) (Components C, respectively component IVa and IVg as shown below):

The resulting memory composition changed colour from green to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Preparation of the Measuring Samples 10 parts of the thermochromic colour memory composition of the water dispersion obtained in Example 1 in encapsulated form were dispersed in 10 parts of a polyvinyl alcohol solution was screen printed onto sheet of copy paper, thereby obtaining a test sample.

The same method has been carried out in order to obtain a test sample for the thermochromic colour memory composition of Examples 2 to 13 in encapsulated form. Each of the test samples was heated and cooled by the below described method, The measuring sample thus prepared was set on a predetermined position of a Linkam (manufactured by linkam, UK) and the colour density at each temperature was measured by heating and cooling at a rate of 5° C./min with a temperature width of 100° C.

For example, in the case of Example 1, the sample was heated up to 100° C. at a rate of 5° C./min from a measurement starting temperature of 0° C., and then cooled to −20° C. at a rate of 5° C./min. The brightness of the colour displayed at each temperature was plotted on a graph to prepare the colour density-temperature curve as illustrated in FIG. 1, and each of $T_1$, T2, T3, $T_4$, and ΔH was obtained.

The results of the temperature analysis in ° C. of the microcapsules is reported below as per their temperature of full clearing (T4) and temperature of full colour return (T1) as well as practical hysteresis ΔH. The results are reported below for the Components C) with different $R_1$ groups as shown in the formula below.

| Example | T1 | T2 | T3 | T4 | ΔH |
|---|---|---|---|---|---|
| Example 1 | −20 | −5 | 55 | 71 | 60 |
| Example 2 | 4 | 18 | 60 | 78 | 42 |
| Example 3 | 30 | 40 | 75 | 87 | 35 |
| Example 4 | −20 | −15 | 55 | 71 | 70 |
| Example 5 | −25 | −10 | 43 | 70 | 53 |
| Example 6 | −18 | −10 | 45 | 70 | 55 |
| Example 7 | −20 | −10 | 40 | 67 | 50 |
| Example 8 | −15 | −10 | 55 | 73 | 65 |
| Example 9 | 2 | 19 | 45 | 72 | 26 |
| Example 10 | 20 | 27 | 55 | 82 | 28 |
| Example 11 | −20 | −15 | 35 | 60 | 50 |
| Example 12 | 18 | 21 | 55 | 65 | 34 |
| Example 13 | −3 | 2 | 45 | 60 | 43 |
| Example 14 | −20 | −16 | 45 | 65 | 61 |

The invention claimed is:

1. A compound of formula (I):

$$[R1X1]_x \underset{Y1}{\underset{|}{\bigcirc}} [CR3R4 \underset{Y3}{\underset{|}{\bigcirc}}]_m [CR5R6]_b \underset{Y4}{\underset{|}{\bigcirc}} \underset{Y2}{\underset{|}{\bigcirc}} [X2R2]_y$$

wherein:
   $R_1$, and $R_2$ are independently selected from an optionally substituted linear or branched alkyl group, alkenyl group, alkoxy group, aryl group and an alkylene aryl group having from 5 to 22 carbon atoms;
   $X_1$ and $X_2$ are both —OC(O)—, such that R1X1 and R2X2 are, respectively, R1C(=O)—O— and R2C(=O)—O—;
   $R_3$, $R_4$ and $R_5$ are independently selected from hydrogen and an optionally substituted linear or branched alkyl group, cycloalkyl group, alkenyl group and alkoxy group;
   $R_6$ is selected from hydrogen, halogen, $R_3$ and —$X_1R_1$ provided that $R_1$ is not aryl, alkenyl or an alkylene aryl group;
   $Y_1$, $Y_2$, $Y_3$ and $Y_4$ are independently selected from hydrogen, halogen, $R_3$, —$OR_3$ provided that —$OR_3$ is not —O-alkenyl; and
   a is 1 to 4; b is 0 or 1; x and y are independently selected from 0 or 1 provided that at least one of x and y is 1.

2. A compound according to claim 1 wherein $R_1$, and $R_2$ are independently selected from $C_{5-22}$ alkyl and phenyl.

3. A compound according to claim 1 wherein $R_1$, and $R_2$ are independently selected from $C_9$ to $C_{17}$ alkyl and phenyl.

4. A compound according to claim 1 wherein $R_3$, $R_4$ and $R_5$ are independently selected from hydrogen and $C_{1-10}$ alkyl.

5. A compound according to claim 1 wherein $R_6$ is selected from hydrogen, $C_{1-10}$ alkyl —OC(O)$R_1$ and —$CO_2R_1$.

6. A compound according to claim 1 wherein $Y_1$, $Y_2$, $Y_3$ and $Y_4$ are independently selected from hydrogen and $C_{1-4}$ alkyl.

7. A compound according to claim 1 wherein a is 1.

8. A compound according to claim 1 wherein the compound (I) has a formula (II):

$$R1X1 \underset{Y1}{\underset{|}{\bigcirc}} CR3R4 \underset{Y3}{\underset{|}{\bigcirc}} \underset{Y4}{\underset{|}{\bigcirc}} CR5R6 \underset{Y2}{\underset{|}{\bigcirc}} X2R2$$

wherein $R_3$, $R_4$, $R_5$ and $R_6$ are independently selected from hydrogen and $C_{1-10}$ alkyl.

9. A compound according to claim 8 wherein $R_3$, $R_4$, $R_5$ and $R_6$ are independently selected from hydrogen and $C_{1-4}$ alkyl group.

10. A compound according to claim 8 wherein $R_3$, $R_4$, $R_5$ and $R_6$ are all methyl.

11. A compound according to claim 8 wherein the moieties —$CR_3R_4$— and —$CR_5R_6$— are in a meta or para relationship to each other.

12. A compound according to claim 8 wherein the moieties —$CR_3R_4$— and $R_1X_1$— and the moieties —$CR_5R_6$ and $R_2X_2$— respectively are in a para relationship to each other.

13. A compound according to claim 8 wherein which $Y_1$, $Y_2$, $Y_3$ and $Y_4$ are all hydrogen, $R_1$ and $R_2$ are independently selected from $C_9$ to $C_{15}$ alkyl and $X_1$ and $X_2$ are —OCO—.

14. A method of making a colour-change composition, said method comprising utilizing a compound of formula (I):

$$[R1X1]_x \underset{Y1}{\underset{|}{\bigcirc}} [CR3R4 \underset{Y3}{\underset{|}{\bigcirc}}]_a [CR5R6]_b \underset{Y4}{\underset{|}{\bigcirc}} \underset{Y2}{\underset{|}{\bigcirc}} [X2R2]_y$$

wherein:
   R1, and R2 are independently selected from an optionally substituted linear or branched alkyl group, alkenyl group, alkoxy group, aryl group and an alkylene aryl group having from 5 to 22 carbon atoms;
   X1 and X2 are independently selected from —OC(O)—, —CO2- and —O—, provided that $R_1X_1$ and $R_2X_2$ are not —O-alkenyl;
   R3, R4 and R5 are independently selected from hydrogen and an optionally substituted linear or branched alkyl group, cycloalkyl group, alkenyl group and alkoxy group;

R6 is selected from hydrogen, halogen, R3 and —X1R1 provided that R1 is not aryl, alkenyl or an alkylene aryl group;

Y1, Y2, Y3 and Y4 are independently selected from hydrogen, halogen, R3, —OR3 provided that —OR3 is not —O-alkenyl; and a is 1 to 4; b is 0 or 1; x and y are independently selected from 0 or 1 provided that at least one of x and y is 1.

15. The method according to claim 14 wherein the colour-change composition is a thermochromic composition.

16. A colour-change composition comprising: A) an electron donating organic colouring compound, B) an electron accepting compound and C) a compound of formula (I):

wherein:
R1, and R2 are independently selected from an optionally substituted linear or branched alkyl group, alkenyl group, alkoxy group, aryl group and an alkylene aryl group having from 5 to 22 carbon atoms;

X1 and X2 are independently selected from —OC(O)—, —CO2- and —O—, provided that $R_1X_1$ and $R_2X_2$ are not —O-alkenyl;

R3, R4 and R5 are independently selected from hydrogen and an optionally substituted linear or branched alkyl group, cycloalkyl group, alkenyl group and alkoxy group;

R6 is selected from hydrogen, halogen, R3 and —X1R1 provided that R1 is not aryl, alkenyl or an alkylene aryl group;

Y1, Y2, Y3 and Y4 are independently selected from hydrogen, halogen, R3, —OR3 provided that —OR3 is not —O-alkenyl; and a is 1 to 4; b is 0 or 1; x and y are independently selected from 0 or 1 provided that at least one of x and y is 1.

17. A colour-change composition according to claim 16 wherein component A) is selected from the group consisting of 3-(4-diethylamino-2-hexyloxyphenyl)-3-(1-ethyl-2-methylindol-3-yl)-4-azaphthalide, 3,3-bis(1-n-butyl-2-methylindol-3-yl)phthalide, 6'-(diethylamino)-2'-(phenylamino)-3H-spiro[2-benzofuran-1,9'-xanthen]-3-one, 2'-chloro-6'-diethylaminofluoran and 2-(2-chloroanilino)-6-di-n-butylaminofluoran.

18. A colour-change composition according to claim 16 wherein component B) is selected from the group consisting of 2,2-bis(4'-hydroxyphenyl) hexafluoropropane, 4,4'-Cyclohexylidenebisphenol 1,1-bis(4'-hydroxyphenyl)-2-methylpropane and mixtures thereof.

19. A colour-change composition according to claim 16 which has a hysteresis range from 10 to 80° C.

20. A colour-change composition according to claim 16 which has a fully decolorized temperature T4 higher than ambient temperature and a fully coloured temperature T1 lower than 20° C.

21. A colour-change composition according to claim 16 further comprising a non-ionic surfactant.

22. A colour-change composition according to claim 21 wherein the non-ionic surfactant is selected from an alcohol alkoxylate, an amine alkoxylate and an end-capped derivative thereof.

23. A colour-change microencapsulated pigment comprising a colour-change composition according to claim 16.

24. A colour-change composition according to claim 16 or a colour-change microencapsulated pigment comprising a colour-change composition according to claim 16, wherein component C) is such that the said colour-change composition or pigment comprising said colour-change composition has a T2 temperature, minimum discoloured state retaining temperature, at 0° C. and a T3 temperature, maximum colour-retaining temperature, above 50° C.

25. An ink composition for a writing implement which comprises a colour-change microencapsulated pigment according to claim 23.

26. A method of making an article selected from the group of toys, printed materials, decoration, writing instruments, temperature indicators in packaging of medical products or in an industrial application, said method utilizing the colour-change composition according to claim 16 or a colour change microencapsulated pigment comprising the colour-change composition.

27. A writing implement comprising a writing device in combination with an ink composition according to the claim 25.

28. A writing implement according to claim 27 comprising a writing device adapted to receive an ink composition and an ink composition for charging to the writing device, said ink composition comprising the colour-change microencapsulated pigment comprising the colour-change composition comprising: A) the electron donating organic colouring compound, B) the electron accepting compound and C) the compound.

29. A method of making the colour change microencapsulated pigment according to claim 23, which has a coloured state and a clear state to provide increased stability against colour change when the composition or pigment is subjected to pressure in the clear state, said method comprising utilizing a non-ionic surfactant.

30. The method according to claim 29 wherein the non-ionic surfactant is selected from an alcohol alkoxylate, an amine alkoxylate and an end-capped derivative thereof.

* * * * *